United States Patent [19]

Clozel et al.

[11] Patent Number: 5,696,116
[45] Date of Patent: Dec. 9, 1997

[54] PHARMACEUTICAL COMPOSITION WHICH CONTAINS A RENIN ANGIOTENSIN SYSTEM INHIBITOR AND AN ENDOTHELIN ANTAGONIST

[75] Inventors: Jean-Paul Clozel; Martine Clozel, both of St. Louis, France; Wolfgang Robert Osterrieder, deceased, late of Grenach-Wyhlen, Germany, by Cornelia Osterrieder, Anne Osterrieder, Stefan Osterrieder, legal heirs

[73] Assignee: Hoffmann-La Roche Inc., Nutley, N.J.

[21] Appl. No.: 273,663

[22] Filed: Jul. 12, 1994

[30] Foreign Application Priority Data

Jul. 15, 1993 [CH] Switzerland ............... 2131/93

[51] Int. Cl.$^6$ ............ A61K 31/505; A61K 31/55; A61K 38/04
[52] U.S. Cl. ............ 514/221; 514/11; 514/16; 514/17; 514/18; 514/19; 514/269
[58] Field of Search ............ 530/860; 514/11, 514/16, 17, 18, 19, 221, 269, 929

[56] References Cited

U.S. PATENT DOCUMENTS

| | | | |
|---|---|---|---|
| 4,248,883 | 2/1981 | Sawayama et al. | 548/336 |
| 4,337,201 | 6/1982 | Petrillo, Jr. | 548/413 |
| 4,374,829 | 2/1983 | Harris et al. | 514/21 |
| 4,385,051 | 5/1983 | Oka et al. | 424/177 |
| 4,410,520 | 10/1983 | Watthey | 514/212 |
| 4,470,972 | 9/1984 | Gold et al. | 514/19 |
| 4,658,024 | 4/1987 | Attwood et al. | 514/221 |
| 4,859,665 | 8/1989 | Garthoff, et al. | 514/221 |
| 5,324,839 | 6/1994 | Clemence et al. | 546/175 |
| 5,338,726 | 8/1994 | Shiosaki et al. | 514/18 |
| 5,378,715 | 1/1995 | Stein et al. | 514/329 |
| 5,420,123 | 5/1995 | Murugesan | 514/220 |

FOREIGN PATENT DOCUMENTS

| | | |
|---|---|---|
| 334 164 | 9/1989 | European Pat. Off. |
| 498723 | 8/1992 | European Pat. Off. |
| 524 512 | 1/1993 | European Pat. Off. |
| 526708 | 2/1993 | European Pat. Off. |
| 2102412 | 2/1983 | United Kingdom. |

OTHER PUBLICATIONS

Thomas Hedner et al., Journal of Hypertension, vol. 10, Supp. 7, pp. 121–132, (1992).
Abstract (corresponding to EP 0065301, Nov. 1982).

Primary Examiner—Jeffrey E. Russel
Attorney, Agent, or Firm—George W. Johnston; Ellen Ciambrone Coletti

[57] ABSTRACT

A pharmaceutical composition suitable for the treatment of cardiovascular disorders is described which comprises an inhibitor of the Renin Angiotensin System and an endothelin antagonist.

6 Claims, 8 Drawing Sheets

PHARMACEUTICAL COMPOSITION WHICH CONTAINS A RENIN ANGIOTENSIN SYSTEM INHIBITOR AND AN ENDOTHELIN ANTAGONIST

BRIEF SUMMARY OF INVENTION

The invention relates to a pharmaceutical composition suitable for the treatment of cardiovascular disorders which comprise an inhibitor of the Renin Angiotensin System and an endothelin antagonist.

DETAILED DESCRIPTION OF THE INVENTION

Figure 1A:
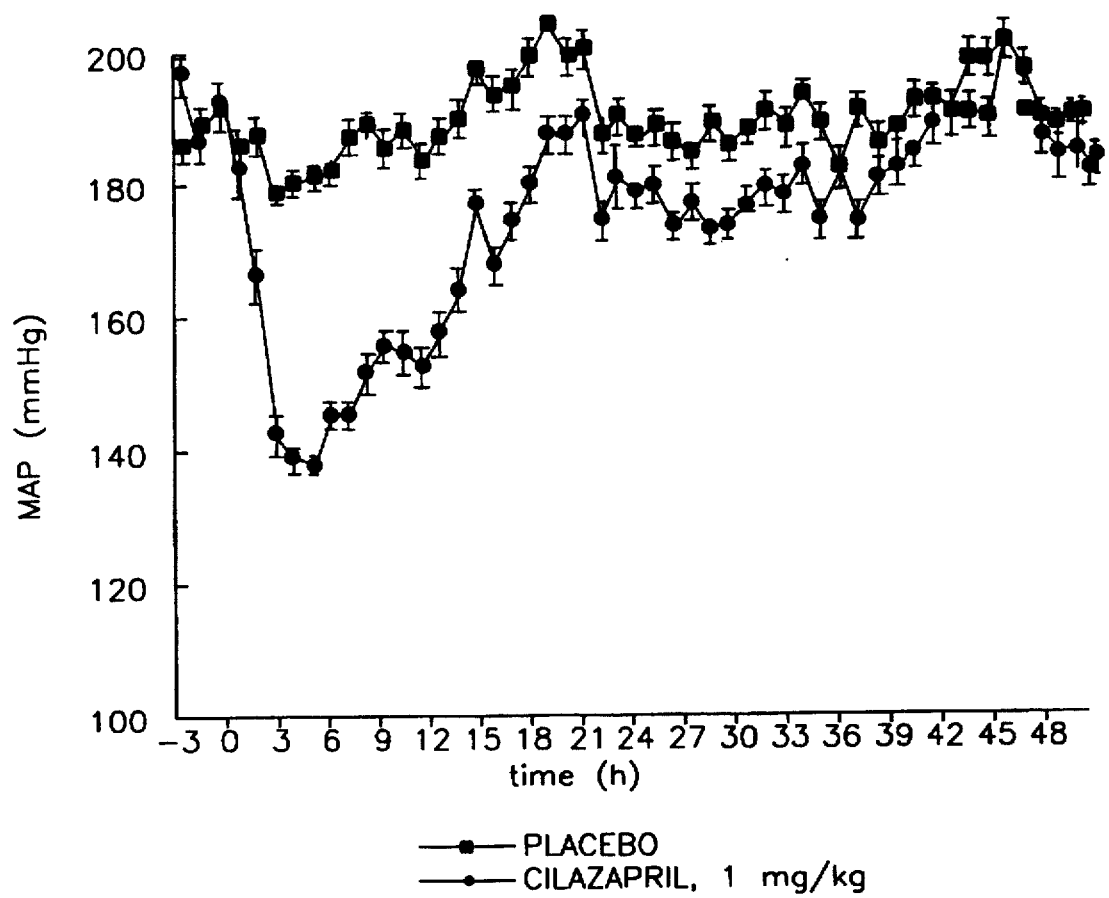
FIGS. 1A–1C and 2A–2C are graphs of average values of blood pressure over time, in animals administered an angiotensin converting enzyme cilazapril and various concentrations of an endothelin antagonist Compound A, alone and in combination.

The renin angiotensin system plays an important role in the regulation of blood pressure. It can be described as a proteolytic cascade which is divided into the following steps:

1. The enzyme renin cleaves angiotensinogen into angiotensin I which is biologically inactive;

2. Angiotensin I is converted into angiotensin II by the enzyme Angiotensin Convening Enzyme (ACE); and 3. Angiotensin II binds to receptors in the membrane of effector cells and triggers a biological response.

These biological responses are manifold, for example, contraction of blood vessels, aldosterone biosynthesis and stimulation of vascular growth after damage.

The renin angiotensin system can be inhibited in all three of the steps described above, namely, in the first, by the use of a renin inhibitor, in the second by the use of an ACE inhibitor and, in the third, by the use of an angiotensin II receptor antagonist.

ACE inhibitors have acquired great importance in the treatment of high blood pressure and cardiac insufficiency. Captopril is the prototype for-this class of substance. Renin inhibitors and angiotensin II receptor antagonists have hitherto not been marketed, but their development is proceeding worldwide.

Endothelin is a peptide hormone which was first discovered a few years ago [Yanagisawa et al., Nature 332, 411–415 (1988)] and which has hitherto been shown to be a very potent vasoconstrictor. Endothelin is secreted from the endothelial cells which line the blood vessels. Although its concentration in blood plasma is very low, it can be assumed from this that local concentrations between endothelial cells and the adjacent smooth muscle cells of the vessels are substantially higher.

An increased endothelin level in blood plasma is to be found in a series of cardiovascular disorders, such as, hypertension, cardiac insufficiency, ischemia (heart, brain, gastro-intestinal tract and kidney) or vasospasms. The concentration of endothelin in bronchial secretion is increased in patients with asthma. An increased endothelin level in blood plasma is also to be found in migraine attacks.

Endothelin binds to specific receptors of effector cells. Hitherto, at least two sub-types of these receptors, namely, endothelin A and endothelin B receptors, have been described [Lin et al., Proc. Natl. Acad. Sci. USA 88. 3185–3189 (1991) and Sakamoto et al., Biochem. Biophys. Res. Commun. 178, 656–663 (1991)]. Endothelin $_A$ causes vasoconstriction, while the significance of endothelin B has not yet been sufficiently clarified.

Because of the pathophysiological significance of endothelin, there is a need to provide a suitable endothelin antagonist. A series of compounds which inhibit the binding of endothelin to the receptor are described in, for example, European Patent Publications 405,421, 436,189, 457,195, 460,679 and 496,452 as well as J. Antibiotics 45, 74 (1992), FEBS 305, 41 (1992) and Bioch. Biophys. Res. Comm. 185, 630 (1992). These are either substances which have been found in nutrient broths and which practically cannot be prepared in a chemical manner or peptides which most probably will not be suitable for oral use in human beings because of inadequate bioavailability. On the other hand, the endothelin antagonists described in European Patent Publications 510,526 and 526,708 as well as WO 93/08 799 are of simple chemical structure and have the advantage that they can be administered orally.

In the scope of the invention it has been possible to establish that, when the combination, in accordance with the invention, of an inhibitor of the renin angiotensin system and an endothelin antagonist is administered, the blood pressure-lowering properties and the duration of action of the individual components are surprisingly potentiated. As a result, the effective doses of the two individual components can be significantly reduced.

The combination, in accordance with the invention, has the advantage that the amounts of active ingredients to be administered can be significantly reduced and undesired side effects can be eliminated or considerably reduced.

The combination, in accordance with the invention, can be used as an agent for the treatment of disorders which are associated with vasoconstriction or other biological effects of endothelin and/or angiotensin II. Examples of such disorders are high blood pressure, coronary diseases, cardiac insufficiency, renal and myocardial ischemia, renal insufficiency, dialysis, subarachnoid hemorrhage, Raynaud syndrome and pulmonary high pressure. Also included are treatment of gastric and duodenal ulcers as well as of ulcus cruris, in which vasoconstriction is involved.

The combination can also be used in the treatment of atherosclerosis and to prevent restenosis after balloon-induced vascular dilation.

Objects of the invention are therefore a combination of a RAS inhibitor and an endothelin antagonist;

a pharmaceutical composition containing a RAS inhibitor and an endothelin antagonist;

the preparation of a pharmaceutical composition, which comprises bringing a mixture of a RAS inhibitor and an endothelin antagonist into a galenical administration form; and the use of a combination of a RAS inhibitor and an endothelin antagonist or of a pharmaceutical preparation containing a RAS inhibitor and an endothelin antagonist for the simultaneous separate or chronologically spaced, use in the treatment of disorders which are associated with vasoconstriction or other biological activities of endothelin and/or angiotensin II, especially of circulatory disorders, particularly in the control or prevention of hypertension and disorders resulting therefrom, as well as, in the treatment of cardiac insufficiency.

The weight ratio of RAS inhibitor to endothelin antagonist conveniently is in the range of 1:1 to 1:500, preferably 1:1 to 1:100.

Advantageously, the dosage to be administered by means of a combination per day amounts to 2.5 to 10 mg of a RAS inhibitor and 250 to 1000 mg of an endothelin antagonist. In general, the total amount of a RAS inhibitor and an endothelin antagonist to be administered daily amounts to a maximum of 550 mg. When a hydrate or a pharmaceutically usable salt is used, then the above values are to be appropriately adjusted.

Renin inhibitors, ACE inhibitors and angiotensin II antagonists come into consideration as inhibitors of the renin angiotensin system. The use of ACE inhibitors is preferred.

Suitable ACE inhibitors for the purpose of the invention are, for example, alacepril, benazepril, captopril, cilazapril, cilazaprilat, delapril, enalapril, enalaprilat, fosinopril, lisinopril, perindopril, quinapril, ramipril, spirapril, zofenopril and MC 838 [calcium salt of (R-(R,S)-1-(3-((2-((cyclohexylcarbonyl)amino)-1-oxopropyl)thio)-2-methyl-1-oxopropyl)-L-proline] as well as analogues of these compounds as are described in European Patent Publications EPA 7,477, 12,401, 50,800, 51,391, 53,902, 65,301, 72,352, 94,095, 172,552, 211,220 and 271,795, U.S. Pat. Nos. 4,105,776 and 4,316,906, British Patent Specification 2,102,412, as well as, in Tetrahedron Letters, 23, 1677–1680 (1982). Preferred ACE inhibitors, are the compounds stated in the aforementioned publications. Especially preferred ACE inhibitors are the compounds specifically named above. Cilazapril is the most preferred ACE inhibitor.

Suitable renin inhibitors for the purpose of the invention are:

(S)-2-Benzyl-N-[(S)-1-[(1S,2R,3S)-1-cyclohexylmethyl-3-cyclopropyl-2,3-dihydroxypropylcarbamoyl]-2-(imidazol-4-yl)ethyl]-3-[1-methyl-1-(morpholin-4-ylcarbonyl) ethylsulphonylmethyl]propionamide (Ciprokiren);

tert-Butyl (2S)-2-[[(αS)-α-[[(1S)-1-[[(1S, 2S, 4S)-2-hydroxy-1-isobutyl-5-methyl-4-[[(1S,2S)-2-methyl-1-[2-pyridylmethyl)carbamoyl]butyl]carbamoyl]-hexyl]carbamoyl]-2-imidazol-4-ylethyl]methylcarbamoyl]-phenethyl]carbamoyl]-1-pyrrolidinecarboxylate (Ditekiren);

[1S-(1R* ,2S *,3R*)]-N-(3-Amino-3 -methyl-1-oxobutyl)-O-methyl-L-tyrosyl-N-[1-(cyclohexylmethyl)-2,3-dihydroxy-5-methylhexyl]-L-histidinamide (Enalkiren);

(S)-2-tert-Butylsulphonylmethyl-N-[(S)-1-[(1S,2R,3S )-1-cyclo-hexylmethyl-3-cyclopropyl-2,3-dihydroxypropylcarbamoyl]-2-(1H-imidazol-4-yl)methyl]-3-phenylpropionamide (Remikiren);

[R-(R*, S*)]-N-(4-Morpholinylcarbonyl)-L-phenylalanyl-N-[1-(cyclohexylmethyl)-2-hydroxy-3-(1-methylethoxy)-3-oxopropyl]-S-methyl-L-cysteinamide (Terlakiren);

N-[2(R)-Benzyl-N-[2-[2-(2-methoxyethoxy)methoxy]ethyl]-N-methyl-succinamoyl]histidine 1 (S)-cyclohexylmethyl-2(R)-hydroxy-2-[3-ethyl-2-oxo-oxazolidin-5(S)-yl] ethylamide (A 65 317);

N-[2(S)-Benzyl-3-(4-methyl-1-piperazinylsulphonyl) propanoyl]-3-(4-thiazolyl)-L-alanine 1(S)-(cyclohexylmethyl)-2(R),3(S)-dihydroxy-5-methylhexylamide (A 72 517);

N-[2(S)-Amino-1-cyclohexyl-3(R),4(S)-dihydroxy-6-methylhept-1-yl]-2(S)-[1(S)-[4-(methoxymethoxy) piperidin-1-ylcarbonyl]-2-phenylethoxy]hexanamide (A 70 461);

6-Cyclohexyl-4(S)-hydroxy-2(S)-isopropyl-5(S)-[2(S)-[1 (S)-[4-(methoxy-methoxy)piperidin-1-ylcarbonyl]-2-phenylethoxy]hexanamido]-N-(3-morpholinopropyl) hexanamide (A 74 273);

6-Cyclohexyl-4(S)-hydroxy-2(S )-isopropyl-5(S)-[N-[1(S)-[4-(methoxy-methoxy)piperidin-1-ylcarbonyl-]-2-phenylethyl]-L-norleucylamino]-N-(2-methyl-2-morpholinopropyl)hexanamide (A 82 110);

Methyl (3S)-4-cyclohexyl-2-hydroxy-3-[[(2S)-4-methyl-2-[[(2S)-2-(1-oxo-1,3-dihydroisoindol-2-yl)-3-phenylpropionyl]amino]pentanoyl]-amino]butyrate (WAY 121 604);

[R-(R*,S*)]-N-(4-Morpholinylcarbonyl)-L-phenylalanyl]-N-[1-(cyclohexylmethyl)-2-hydroxy-2-(1H-imidazol-2-yl) ethyl]-L-histidinamide (SQ 31 844);

[1S-[1R*(R*),2S*,3S*]]-[2-(tert-Butylsulphonylmethyl)-1-oxo-3-phenylpropyl]-N-[4-[(butylamino)sulphonyl]-1-(cyclohexylmethyl)-2,3-dihydroxybutyl]-L-histidinamide monomethanesulphonate (SQ 33 800);

[1S -(1R * ,2R * ,4S*)]-N-[(1,1-Dimethylethoxy)carbonyl]-L-phenylalanyl-N-[5-[(4-aminobutyl)amino]-1-(cyclohexylmethyl)-2-hydroxy-5-oxo-4-(4-pyridinylmethyl)pentyl]-L-histidinamide (GR 70 982);

(2S,4S,5S)-N-Butyl-6-cyclohexyl-4-hydroxy-2-isopropyl-5-[2-[8-propyl-6-(3-pyridyl)-1,2,4-triazolo[4,3-a]pyrazin-3-yl]-3-(3-pyridyl)propionamido]hexanamide (ICI 219 623);

4-(Boc-Phe-His-ACHPA-Lys-NH-CH₂)pyridine (L 157 119);

[2R-(2R*,4S*, 5S*)]-N-[N2-[6-Cyclohexyl-5-[[N-[N-[(1,1-dimethylethoxy)-carbonyl]-L-phenylalanyl]-L-phenylalanyl]-L-histidyl]amino]-4-hydroxy-2-(2-methylpropyl)-1-oxohexyl]-L-lysyl]-L-phenylalanine diacetate (CP 71 362);

5 -Cyclohexyl-2,4,5-trideoxy-N-hexyl-4-[[N-[3-(1-naphthalenyl)-N-(4-morpholinylacetyl)-L-alanyl]-3-(4-thiazolyl)-L-alanyl]amino]-L-threopentanamide (ES 8 891);

[1S-[1R*(R*),2R*,4[R*(R*)]]]-N-[4-[[1-[[(5-Amino-6-hydroxyhexyl)amino]-carbonyl]-3-methylbutyl]amino]-2-hydroxy-1-(2-methylpropyl)-4-oxobutyl]-α-[[3 -(1-naphthalenyl)-2-(1-naphthalenylmethyl)-1-oxopropyl] amino]-1H-imidazol-4-propanamide (ES 1 005);

[1S -(1R*,2S*,3R*)]-N-(4-Morpholinylsulphonyl)-L-phenylalanyl-N-[1-(cyclohexylmethyl)-2,3 -dihydroxy-5-methylhexyl]-O-methyl-3 -oxo-D- or or L-serinamide (PD 132 002);

([1S -(1R*,2S* ,3R*)])-N-(4-Morpholinylsulphonyl)-L-phenylalanyl-3-(2-amino-4-thiazolyl)-N-[(cyclohexylmethyl)-2,3-dihydroxy-5-methylhexyl]-L-alaninamide (PD 134 674);

N-[2-[[1-(Cyclohexylmethyl)-2-hydroxy-3-[(1-methyl-1H-tetrazol-5-yl)thio]propyl]amino]-1-(1H-imidazol-4-ylmethyl)-2-oxoethyl]-α-(1-naphthalenylmethyl)-γ-oxo-4-morpholinobutanamide (YM 21 095);

N-Methyl-N-[2(S)-[N-methyl-N-[2-[N-methyl-N-(morpholinocarbonyl)amino]ethyl]carbamoyl]-3-phenylpropionyl]-L-histidine1(S)-(cyclohexylmethyl)-2(S)-hydroxy-5-methylhexylamide (FK 906);

Ethyl [1S-[1R*[R*(R*)],2R*]]-methyl[3-(4-morpholinyl)-3-oxopropyl]2-[[2-[[1-(cyclohexylmethyl)-2-hydroxy-5-methylhexyl]amino]-1-(1H-imidazol- 4-ylmethyl)-2-oxoethyl]methylamino]-2-oxo-1-(phenylmethyl) carbamate (FK 744);

3-(4-Aminopiperidin-1-ylcarbonyl)-2(R)-benzylpropionyl-L-histidine 1(S)-(cyclohexylmethyl)-2(R), 3(S)-dihydroxy-5-(2-pyridyl) pentylamide acetate (S 89-2864);

3-Amino-3-methylbutyryl-(4-O-methyl)-L-tyrosyl-L-norvaline 1-(cyclohexylmethyl)-3,3-difluoro-4-(3-methylbutyramido)-2-oxobutylamide hydrochloride hydrate (MDL 73 323); and 1H-Indol-2-ylcarbonyl-L-histidine 1(S)-(cyclohexylmethyl)-2(S),4(S)-dihydroxy-5-methylhexylamide (JTP 3 071).

Suitable angiotensin II antagonists for the purpose of the invention are:

2-Butyl-4-chloro-1-[[2'-(1H-tetrazol-5-yl)[1,1'-biphenyl]-4-yl]methyl]-1H-imidazol-5-methanol potassium salt (Losartan);

N-(1-Oxopentyl)-N-[[2'-(1H-tetrazol-5-yl)[1,1'-biphenyl]-4-yl]methyl]-L-valine (Valsartan);

4'-[(2-n-Butyl-6-cyclohexylaminocarbonylamino-benzimidazol-1-yl)methyl]biphenyl-2-carboxylic acid (BIBS 39);

2-n-Butyl-1-[4-(6-carboxy-2,5-dichlorobenzoylamino)benzyl]-6-N-(methylaminocarbonyl)-n-pentylaminobenzimidazole (BIBS 222);

4'-[(1,4'-Dimethyl-2'-propyl-[2,6'-bi-1H-benzimidazol]-1'-yl)methyl]-[1,1'-biphenyl]-2-carboxylic acid (BIBR 277);

4-(Pentafluoroethyl)-2-propyl-1-[[2'-(1H-tetrazol-5-yl)[1,1'-biphenyl]-4-yl]methyl]-1H-imidazole-5-carboxylic acid (DuP 532);

4'-[[2-Butyl-4-chloro-5-(hydroxymethyl)-1H-imidazol-1-yl]methyl]-[1,1'-biphenyl]-2-carboxylic acid (EXP 7 711);

2-Ethyl-5,6,7,8-tetrahydro-4-([2'-(1H-tetrazol-5-yl)biphenyl-4-yl]methoxy)quinoline (D 6 888);

2-Ethyl-4-[(2'-(1H-tetrazol-5-yl)biphenyl-4-yl)methoxy]quinoline hydrochloride (D 8 731);

1-((3-Bromo-2-(2-(1H-tetrazol-5-yl)phenyl)-5-benzofuranyl)methyl)-2-butyl-4-chloro-1H-imidazole-5-carboxylic acid (GR 117 289);

1-[[3-Bromo-2-[2-[[(trifluoromethyl)sulphonyl]amino]phenyl]-5-benzofuranyl]methyl]-4-cyclopropyl-2-ethyl-1H-imidazole-5-carboxamide (GR 138 950);

5,7-Dimethyl-2-ethyl-3-(2'-(1H-tetrazol-5-yl)(1,1'-biphenyl)-4-yl)methyl)-3H-imidazo(4,5-b)pyridine (L 158 809);

5-[4'-(3,5-Dibutyl-1,2,4-triazol-1-ylmethyl)biphenyl-2-yl]-1H-tetrazol (SC 50 560);

1,4-Dibutyl-3-[2'-(1H-tetrazol-5-yl)biphenyl-4-ylmethyl]-2,3-dihydro-1H-imidazol-2-one (SC 51 895);

2-n-Butyl-4-spirocyclopentane-1-[(2'-(1H-tetrazol-5-yl)biphenyl-4-yl)methyl]-2-imidazolin-5-one (SR 47 436);

(E)-α-[[2-Butyl-1-[(4-carboxyphenyl)methyl]-1H-imidazol-5-yl]methylene]-2-thiophenepropanoic acid (SKF 108 566);

2-Ethoxy-1-[[2'-(1H-tetrazol-5-yl)[1,1'-biphenyl]-4-yl]methyl]-1H-benzimidazole-7-carboxylic acid 1-[[(cyclohexyloxy)carbonyl]oxy]ethyl ester (TCV 116/CV 11 974);

2-Propyl-4-[(3-trifluoroacetyl)pyrrol-1-yl]-1-[[2'-(2H-tetrazol-5-yl)[1,1'-biphenyl]-4-yl]methyl]-1H-imidazole-5-carboxylic acid (CI 996); and 2,7-Diethyl-5-[[2'-(1H-tetrazol-5-yl) [1,1'-biphenyl]-4-yl]methyl]-5H-pyrazolo[1,5-b][1,2,4]triazole potassium salt (YM 358).

Peptidic and non-peptidic derivatives come into consideration as endothelin antagonists, with the non-peptidic derivatives being preferred because of the poor bioavailability which must be expected in the case of the peptidic derivatives. Those non-peptidic derivatives which have oral activity are especially preferred. Examples of peptidic derivatives are:

Perhydroazepin-1-ylcarbonyl-L-leucyl-(1-methyl)-D-tryptophyl-[3-(2-pyridyl)]-D-alanine (FR 139 317);

2-Acetamido-3-[[1,4,4a, 5,6,6a,7,12, 12a, 12b-decahydro-4a, 8,12a, 12b-tetrahydroxy-3-methyl-1,7,12-trioxobenz[α]anthracen-6a-yl]thio]propionic acid (FR 901 367);

Cyclo(-D-Trp-D-Glu-L-Ala-allo-D-Ile-L-Leu-) (BE 18 257 B);

Cyclo(-D-Trp-D-Asp-L-Pro-D-Val-L-Leu-) (BQ 123);

Perhydroazepin-1-ylcarbonyl-L-leucyl-D-tryptophyl-D-tryptophan;

Cochinmicin I;

Myricerone caffeic acid ester; and

Acetyl-(3,3-diphenyl-D-alanine)-L-Leu-L-Asp-L-Ile-L-Ile-L-Trp (PD 142 893).

Suitable non-peptidic endothelin antagonists for the purpose of the invention are the sulfonamides and the indane and indene derivatives which are described in European Patent Publications 510,526 and 526,708 or WO 93/08 799, especially the compounds:

4-tert-Butyl-N-[6-(2-hydroxyethoxy)-5-(2-methoxyphenoxy)-2,2'-bipyrimidin-4-yl]benzenesulphonamide;

(1RS, 2SR,3SR)-1-(4-methoxyphenyl)-3-(3,4-methylenedioxyphenyl)indane-2-carboxylic acid;

(1RS ,2RS ,3SR)-5-hydroxy-3-(4-methoxyphenyl)-1-(3,4-methylenedioxyphenyl)indane-2-carboxylic acid;

(1RS ,2RS ,3SR)-5-methoxy-3-(4-methoxyphenyl)-1-(3,4-methylenedioxyphenyl)indane-2-carboxylic acid;

(1RS ,2SR,3SR)-1,3-bis(3,4-methylenedioxyphenyl)-5-hydroxyindane-2-carboxylic acid;

(1RS ,2SR ,3RS )-3-(2-carboxymethoxy-4-methoxyphenyl)-1-(3,4-methylenedioxyphenyl)-5-(prop-1-yloxy)indane-2-carboxylic acid;

(1RS ,2SR,3SR)-3-(2-carboxymethoxy-4-methoxyphenyl)-1-(2-methoxy-4,5-methylenedioxyphenyl)-5-(prop-1-yloxy)indane-2-carboxylic acid;

(1RS,2SR,3RS)-3- [2-(1-carboxyeth-2-yloxy)-4-methoxyphenyl]-1-(3,4-methylenedioxyphenyl)-5-(prop-1-yloxy)indane-2-carboxylic acid bis-dicyclohexylamine salt;

(1RS,2SR,3SR)-[2-[(E)-2-carboxyethen-1-yl]-4-methoxyphenyl]-1-(3,4-methylenedioxyphenyl)-5-(prop-1-yloxy)indane-2-carboxylic acid;

(1RS ,2SR ,3SR)-3-[2-(2-carboxyeth-1-yl)-4-methoxyphenyl]-1-(3,4methylenedioxyphenyl)-5-(prop-1-yloxy)indane-2-carboxylic acid and (1RS,2SR,3RS)-3-[2-(3-carboxyphenyl)-4-methoxyphenyl]-1-(3,4-methylenedioxyphenyl)-5-(prop-1-yloxy)indane-2-carboxylic acid.

Combinations of 4-tert-butyl-N-[6-(2-hydroxyethoxy)-5-(2-methoxyphenoxy)-2,2'-bipyrimidin-4-yl]benzenesulphonamide (also referred to hereinafter as compound A) and cilazapril are of particular interest in accordance with the invention.

A regular and long-lasting blood pressure-lowering activity can be achieved with the combinations of the invention using low doses of active ingredients.

The advantageous synergistic blood pressure-lowering activity as well as the longer duration of activity of the combination of the invention vis-a-vis those of the two individual components, will be evident on the basis of the data presented hereinafter.

Blood pressure-lowering in spontaneous hypertensive rats

A first study was carried out with rats. Rats of the strain SHRSP (weight about 300 g and age 18–20 weeks) were used. SHRSP (sponanteously hypertensive rats, stroke prone) is the commercial designation for spontaneous hypertensive rats which develop a tendency towards cerebral apoplexy, as they age. The blood pressure had stabilized in these rats at the age of 18 weeks.

The arterial blood pressure of these rats was measured using a telemetric method. (Telemetric system by Data Sciences, Inc., St. Paul, Minn., USA). The blood pressure measurement was effected by means of a fluid-filled catheter which had been implanted in the abdominal aorta. The implantation was effected under brief narcosis (15–20 min.) with Evipan® (100 mg/kg intraperitoneally). The catheter was connected to a minitransmitter in the abdominal cavity, which sent the blood pressure variations to a transmitter outside the cage. In this manner, a continuous measurement in freely mobile animals over a long period of time was possible.

The study was carried out with a total number of 9 rats in a crossover design, that is, each of the rats received no substance (only solvent) once, compound A once, cilazapril once and a combination of compound A with cilazapril once. A period of at least 48 hours elapsed between the individual administrations. The dosage was 100 mg/kg orally for compound A and 1 mg/kg orally for cilazapril. The administration was effected with a stomach tube.

Figure 1B:
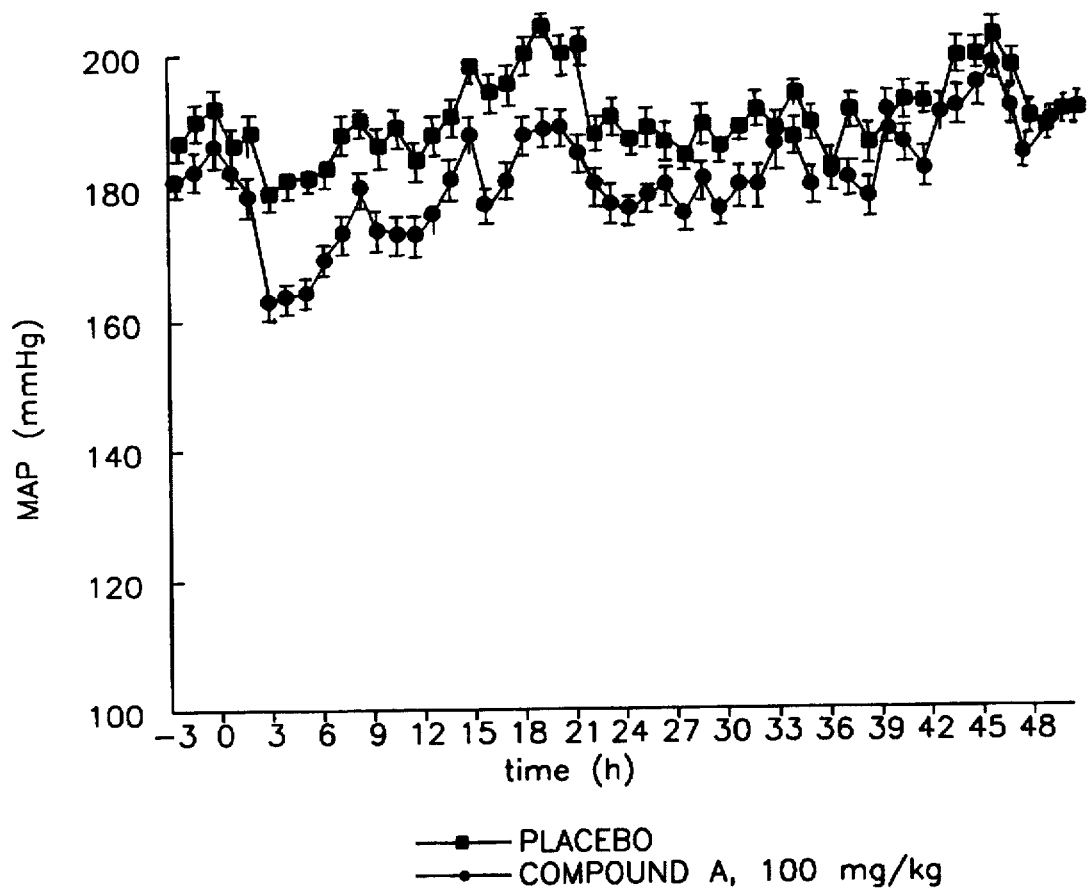
Figure 1C:
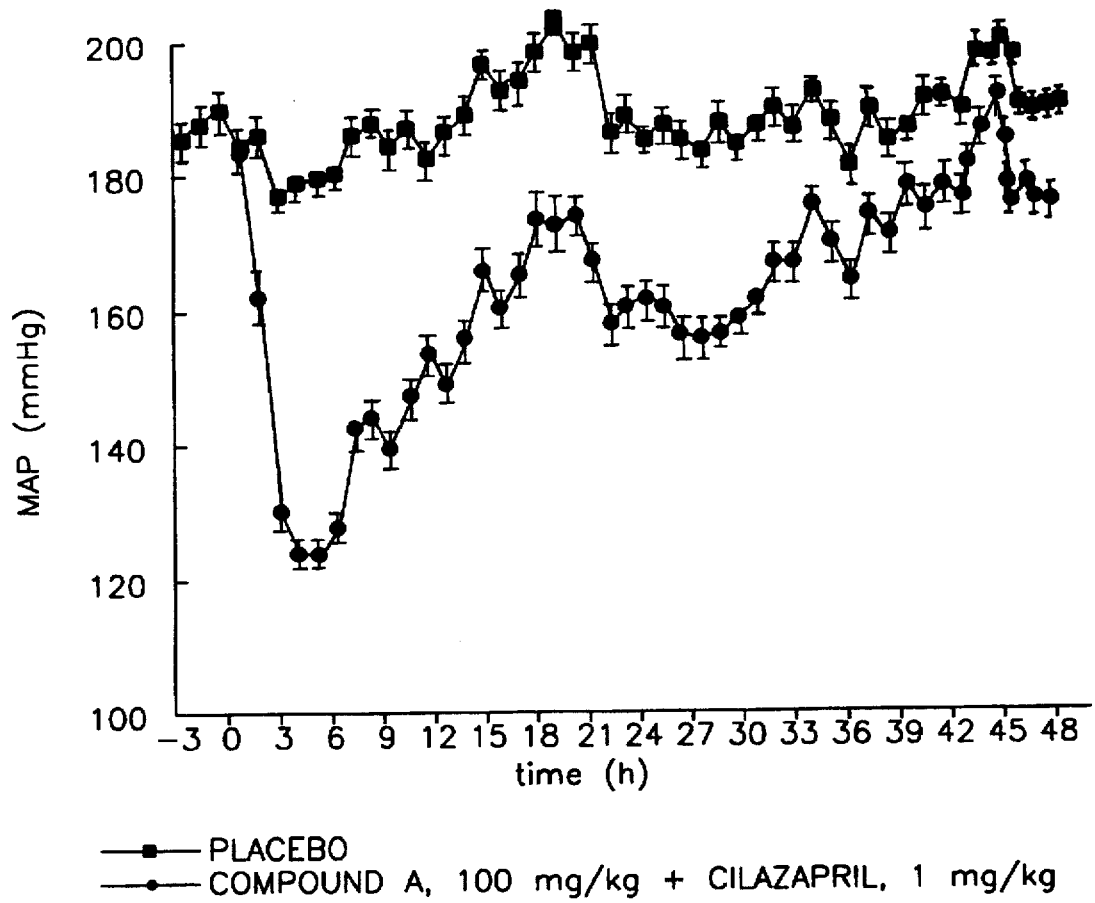

FIGS. 1A–1C summarizes the results of this first series of experiments and illustrates the effect of cilazapril (1 mg/kg p.o.) and compound A (100 mg/kg p.o.) alone, as well as, the effect of the simultaneous administration of the same doses of the two substances (n=9 rats).

Figure 2A:
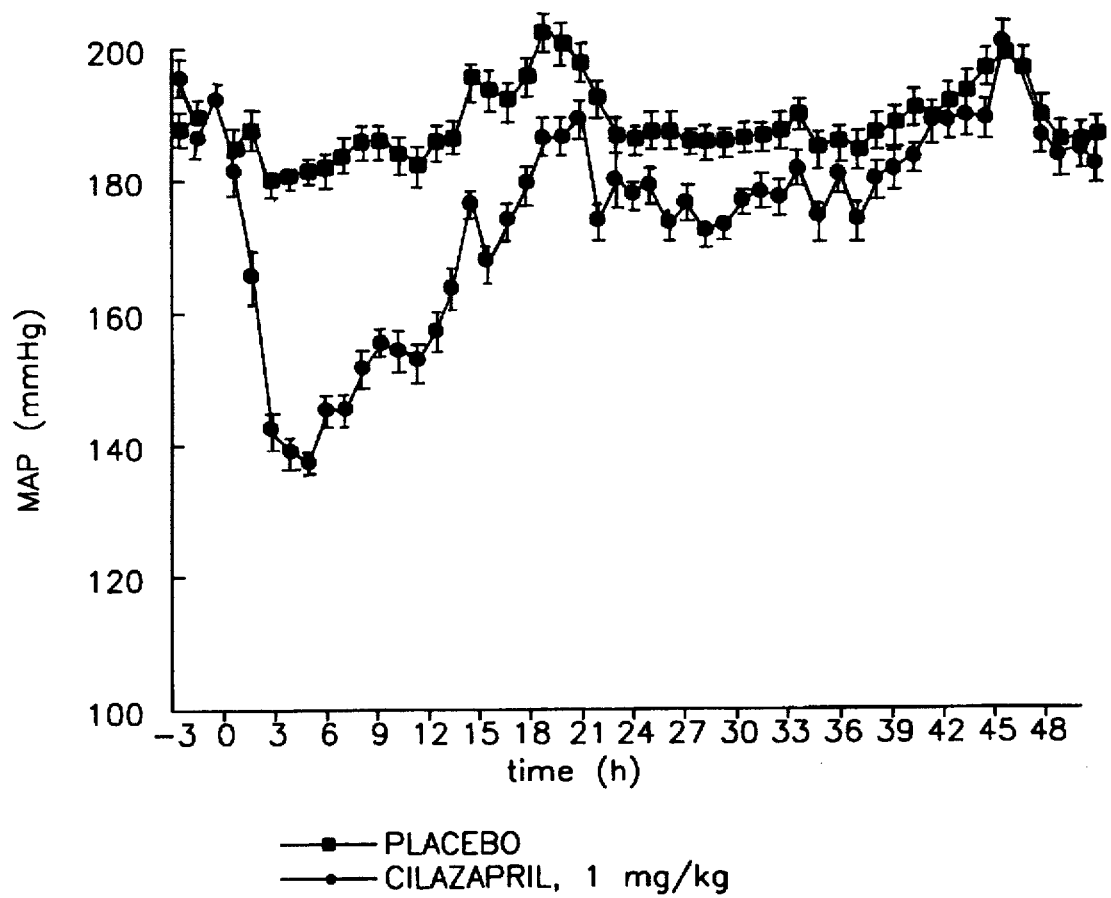
Figure 2B:
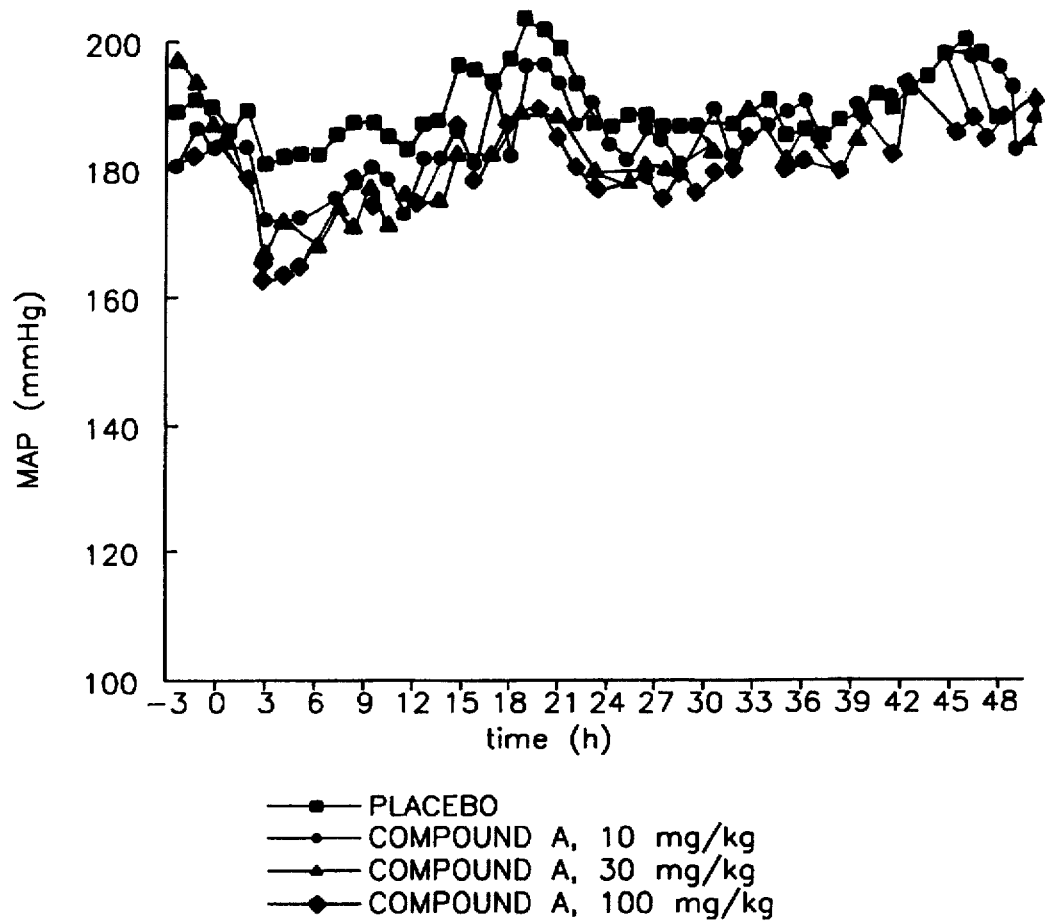
Figure 2C:
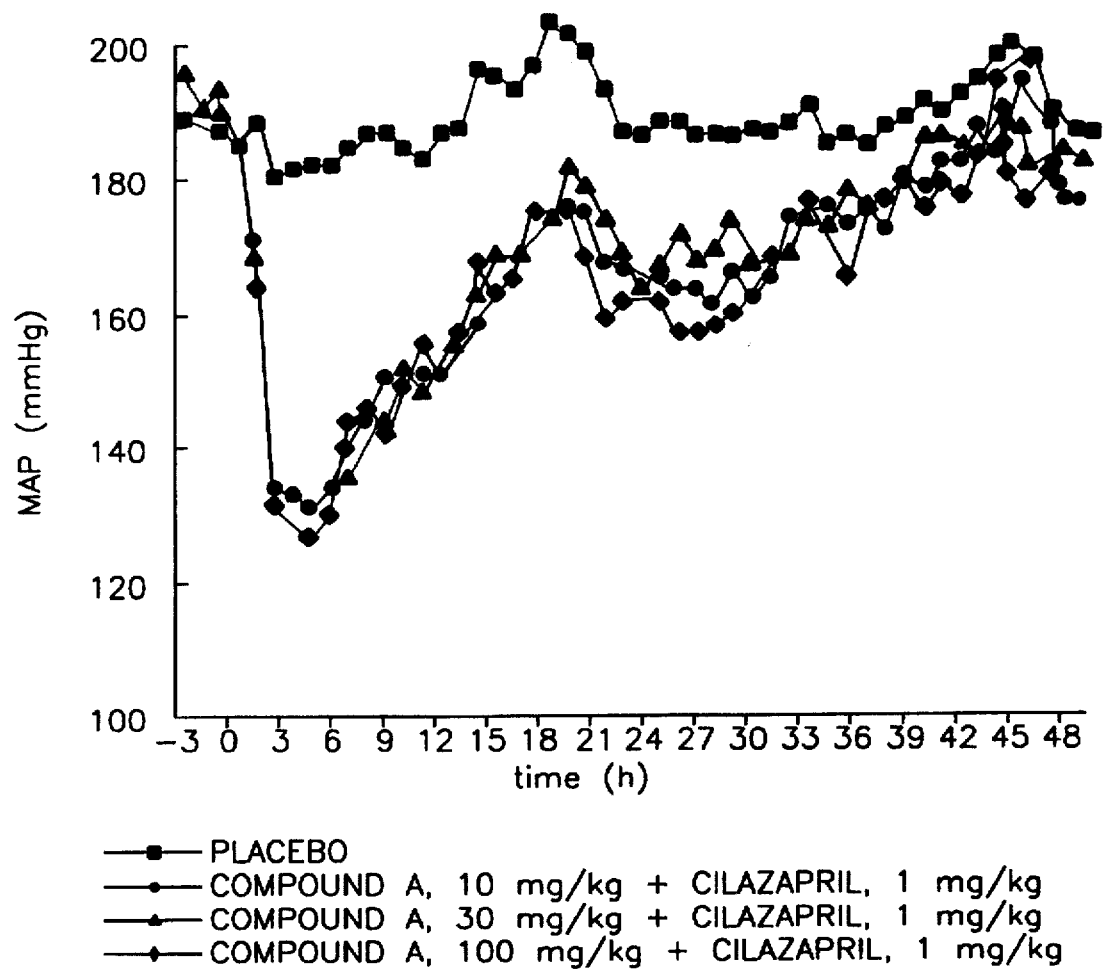

Additional experiments with two other dosages of compound A were, carried out in order to confirm the results obtained, namely, with 10 and 30 mg/kg p.o.. The dose of cilazapril of the first experiment (FIG. 1–C; 1 mg/kg p.o.) .being retained. The results obtained are compiled in FIGS. 2A–2C. The data using cilazapril alone and with 100 mg/kg of compound A, set out in FIGS. 1A–1C, being transferred over into FIGS. 2A–2C.

The values in FIGS. 1A–1C and 2A–2C are the average values of the blood pressure in the 9 experimental animals. The deviation dashes indicate the standard deviation. For clarity, the deviation dashes have been omitted in FIGS. 2-B and 2-C.

Compound A lowered the median arterial blood pressure (MAP) slightly, with the maximum effect being about 20 mmHg (FIG. 2-B). Cilazapril showed the expected pressure lowering, which lasted about 20 hours (maximum effect: blood pressure reduction by about 45 mmHg (FIG. 2-A)). The combination lowered the blood pressure by about a maximum 60 mmHg. Special attention is drawn to the fact that after 20 hours a significant effect could still be observed. Even after 40 hours the same effect as with cilazapril alone after 20 hours could be observed (FIG. 2-C).

The two low dosages of compound A acted similarly to the high dosage of compound A (FIG. 2-B). The lengthening of activity could be confirmed.

Blood pressure lowering in normotensive monkeys

The effect of compound A in combination with the renin inhibitor remikiren was investigated in a second study. Monkeys were used for this study, since remikiren is specific for primate renin and is therefore not active in rats. Remikiren is a potent renin inhibitor with oral availability (Fischli et al., Hypertension 18, 22–31 (1991)).

The measured variable was the arterial blood pressure, which was likewise measured telemetrically. The monkeys of the species Saimiri sciureus (squirrel monkeys) weighed 400–700 g. The reactivity of the blood pressure to RAS inhibitor was increased by sodium depletion. The sodium depletion was achieved by the subcutaneous injection of 5 mg/kg of furosemide (Lasix®) 66, 42 and 18 hours prior to the beginning of the experiment. The animals received no feed in the night prior to the experiment. During the experiment, the monkeys were kept in a separate room and monitored with video cameras, in order to avoid stress caused by the experimenters, with resulting blood pressure variations.

Figure 3:
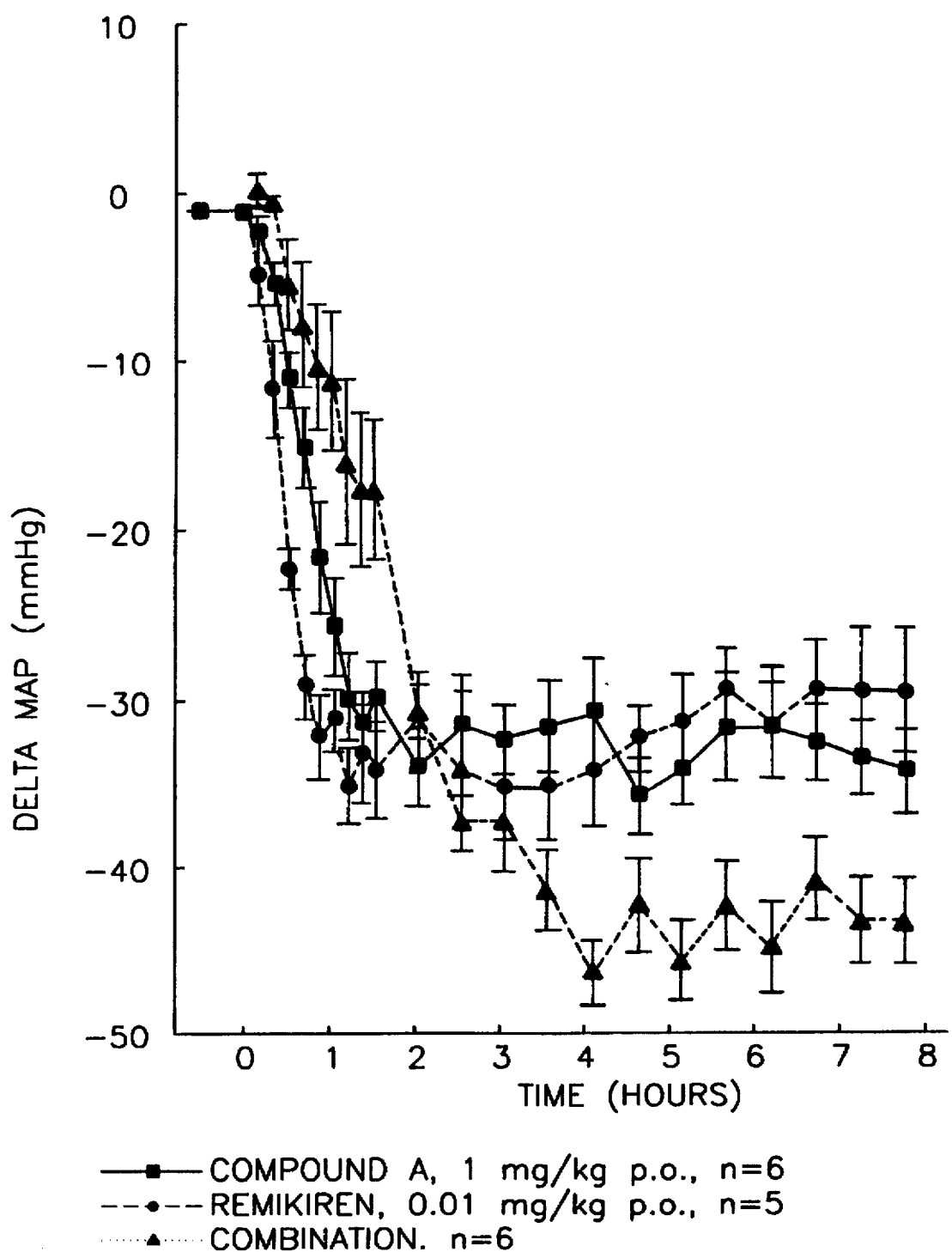
FIG. 3 is a graph of changes of the average blood pressure over time, in animals administered the renin inhibitor remikiren and the endothelin antagonist, Compound A, alone or in combination.

FIG. 3 summarizes the results of this experiment, with each of the changes of the average blood pressure, which was 100 mmHg, being given. Compound A in a dosage of 1 mg/kg p.o. (n=6 monkeys) and 0.01 mg/kg remikiren (n=5 monkeys) lowered the blood pressure by about 30 mmHg, in each case. The combination was significantly more effective. Since, for reasons of good animal practice, it is not possible to keep the monkeys in the measurement cage for longer than 8 hours, no conclusion can be drawn with respect to the duration of activity.

Cardiac insufficiency

Figure 4:
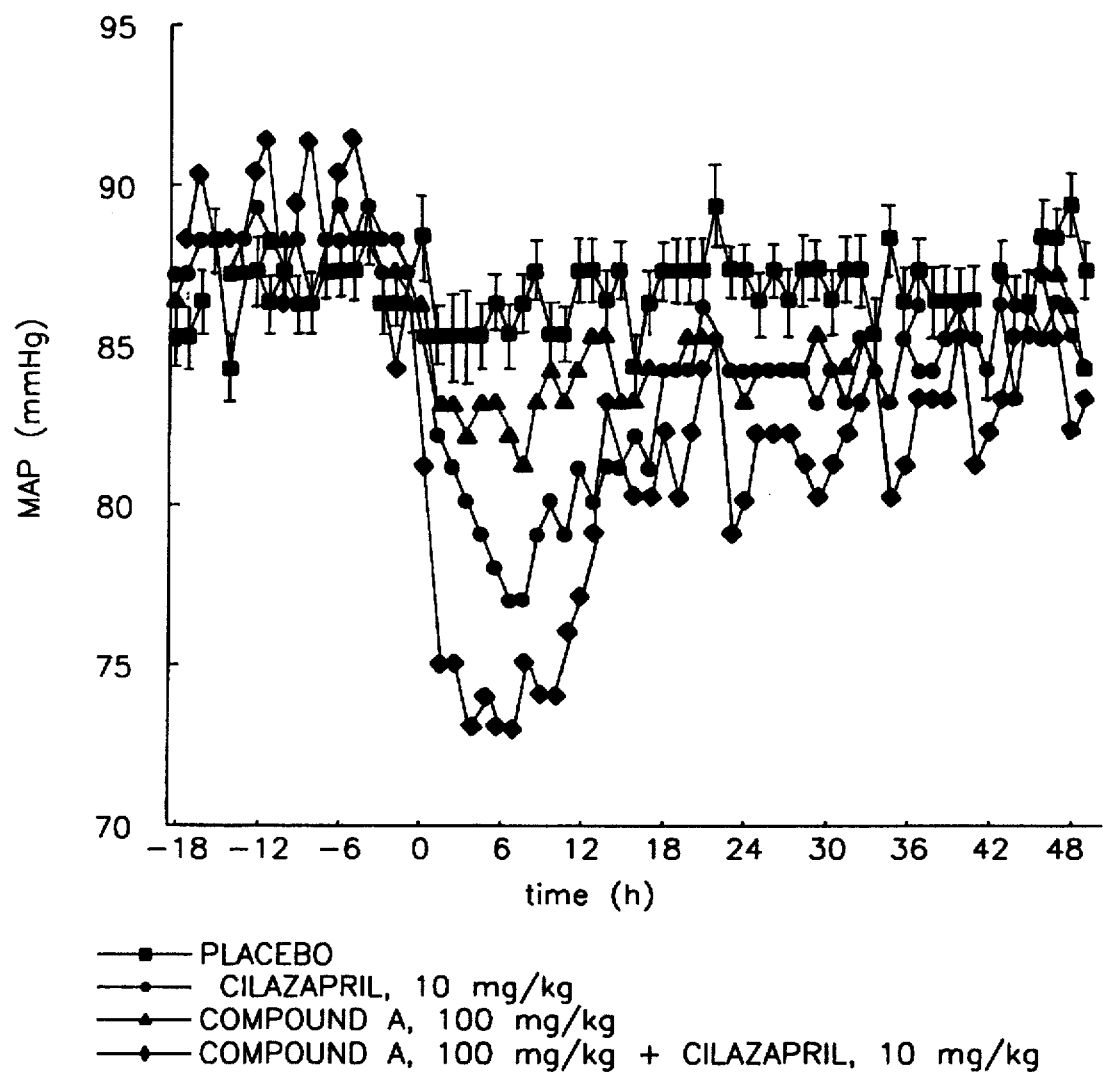
FIG. 4 is a graph of arterial blood pressure over time in animals administered cilazapril and compound A, alone or in combination.

Since ACE inhibitors are today used in standard therapy of patients with cardiac insufficiency, compound A and cilazapril were also tested alone and in combination in an animal model for cardiac insufficiency. Rats were used in which 8 weeks, after a coronary ligature (A. circumflex) the symptoms of complete cardiac insufficiency had appeared. The arterial blood pressure was measured telemetrically, as described above. The results of this experiment are compiled in FIG. 4. In order to make the presentation clearer, the deviation dashes have only been marked in the placebo curve. The intensified and lengthened activity of the combination compared to the individual components was also confirmed in this animal model.

The foregoing results show the unexpectedly advantageous properties of the combinations in accordance with the invention.

The combinations, in accordance with the invention, are generally administered orally, for example, in the form of tablets, coated tablets, dragées, hard and soft gelatine capsules, solutions, emulsions or suspensions. The administration can, however, also be effected rectally, for example, in the form of suppositories, or parenterally, for example, in the form of injection solutions. The administration of the active substances can be effected in the form of preparations which comprise the two active substances in one unit dosage form, such as tablets or capsules, or separately as an ad-hoc combination in unit dosage forms, simultaneously or chronologically spaced.

A combination in accordance with the invention can be processed with pharmaceutically inert, inorganic or organic excipients for the manufacture of tablets, coated tablets, dragées and hard gelatine capsules. Lactose, corn starch Or derivatives thereof, talc, stearic acid or its salts, and the like, can be used as such excipients, for example, for tablets, dragées and hard gelatine capsules.

Suitable excipients for soft gelatin capsules are, for example, vegetable oils, waxes, fats, semi-solid and liquid polyols, and the like; depending on the nature of the active ingredient. No excipients are, however, usually required in the case of soft gelatin capsules.

Suitable excipients for the preparation of solutions and syrups are, for example, water, polyols, saccharose, invert sugar, glucose and the like.

Suitable excipients for injection solutions are, for example, water, alcohols, polyols, glycerol, vegetable oils, and the like.

Suitable excipients for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or anti-oxidants. They can also contain still other therapeutically valuable substances.

The following Examples illustrate the invention.

EXAMPLE 1

Preparation of varnished tablets of the following composition:

Varnished tablet core:

| | | |
|---|---|---|
| a. | Compound A* | 500.0 mg |
| b. | Cilazapril | 5.0 mg |
| c. | Anhydrous lactose | 30.0 mg |
| d. | Microcrystalline cellulose | 30.0 mg |
| e. | Polyvinylpyrrolidone | 20.0 mg |
| f. | Magnesium stearate | 5.0 mg |
| | Weight per varnished tablet core | 590.0 mg |

*4-tert-butyl-N-[6-(2-hydroxyethoxy)-5-(2-methoxyphenoxy)-2,2'-bipyrimidin-4-yl]benzenesulphonamide Preparation of the varnished tablet core:

Compound A, cilazapril, the lactose, the cellulose and the polyvinylpyrrolidone are mixed and sieved. The mixture is moist granulated, dried and sieved. The sieved granulate is mixed with the magesium stearate and the finished press mixture is pressed to oval tablet cores of 590.0 mg.

Varnish coating:

| | | |
|---|---|---|
| g. | Hydroxypropylmethylcellulose | 3.5 mg |
| h. | Ethylcellulose | 3.5 mg |
| i. | Polyethylene glycol 6000 | 0.8 mg |
| j. | Yellow iron oxide | 1.2 mg |
| k. | Titanium dioxide | 0.3 mg |
| l. | Talc | 0.7 mg |
| | Varnish coating weight | 10.0 mg |
| | Total weight per varnished tablet | 600.0 mg |

Preparation of the varnish coating:

An aqueous varnish suspension is prepared from the ingredients, g to 1, and the varnished tablet cores are coated therewith in a suitable manner with the aid of a varnishing procedure in a dragéeing kettle or another varnishing apparatus until the varnished tablets have achieved a final weight of 600 mg.

EXAMPLE 2

Preparation of hard gelatin capsules of the following composition:

| | | |
|---|---|---|
| a. | Compound A* | 250.0 mg |
| b. | Cilazapril | 2.5 mg |
| c. | Cryst. lactose | 18.0 mg |
| d. | Polyvinylpyrrolidone | 15.0 mg |
| e. | Microcrystalline cellulose | 17.5 mg |
| f. | Sodium carboxymethylstarch | 10.0 mg |
| g. | Talc | 9.0 mg |
| h. | Magnesium stearate | 3.0 mg |
| | Fill weight per capsule | 325.0 mg |

*4-tert-butyl-N-[6-(2-hydroxyethoxy)-5-(2-methoxyphenoxy)-2,2'bipyrimidin-4-yl]benzenesulphonamide Compound A, cilazapril, the lactose, the polyvinylpyrrolidone and the cellulose are sieved and mixed. The mixture is moist granulated and dried. The granulate is mixed with the sodium carboxymethyl starch, the talc and the magnesium stearate and the ready-to-fill final mixture is filled into hard gelatin capsules of size 1.

It is claimed:

1. A pharmaceutical composition which comprises 4-tert-butyl-N-[6-(2-hydroxyethoxy)-5-(2-methoxyphenoxy)-2,2'-bipyrimidin-4-yl]benzenesulfonamide and cilazapril, wherein the weight ratio of cilazapril to 4-tert-butyl-N-[6-(2-hydroxyethoxy)-5-(2-methoxy phenoxy)-2,2'-bipyrimidin-4-yl]benzenesulfonamide is 1:1 to 1:500.

2. A pharmaceutical composition according to claim 1, wherein the weight of cilazapril is 2.5 to 10 mg and the weight of 4-tert-butyl-N-[6-(2-hydroxyethoxy)-5-(2-methoxyphenoxy-2,2'-bipyrimidin-4-yl]benzenesulfonamide is 250 to 1000 mg.

3. A pharmaceutical composition according to claim 2, wherein the total weight of cilazapril and 4-tert-butyl-N-[6-(2-hydroxy-ethoxy)-5-(2-methoxphenoxy-2,2'-bipyrimidin-4-yl]benzene-sulfonamide is a maximum of 550 mg.

4. A method for the treatment of disorders associated with vasoconstriction which comprises administering to a host in need of such treatment a pharmaceutical composition comprising cilazapril and 4-tert-butyl-N-[6-(2-hydroxyethoxy)-5-(2-methoxyphenoxy)-2,2'-bipyrimidin-4-yl]benzenesulfonamide, wherein the weight ratio of cilazapril to 4-tert-butyl-N-[6-(2-hydroxyethoxy)-5-(2-methoxyphenoxy)-2,2'-bipyrimidin-4-yl]benzenesulfonamide is 1:1 to 1:500.

5. A method according to claim 4, wherein the weight of cilazapril is 2.5 to 10 mg and the weight of 4-tert-butyl-N-[6-(2-hydroxyethoxy)-5-(2-methoxyphenoxy)-2,2'-bipyrimidin-4-yl]benzenesulfonamide is 250 to 1000 mg.

6. A method according to claim 5, wherein the total weight of cilazapril and 4-tert-butyl-N-[6-(2-hydroxyethoxy)-5-(2-methoxyphenoxy)-2,2'-bipyrimidin-4-yl]benzene sulfonamide is a maximum of 550 mg.

* * * * *